United States Patent [19]

Bunnelle et al.

[11] 4,418,123
[45] Nov. 29, 1983

[54] EXTRUDABLE SELF-ADHERING ELASTIC AND METHOD OF EMPLOYING SAME

[75] Inventors: William L. Bunnelle, Stillwater; Richard C. Lindmark, Coon Rapids, both of Minn.

[73] Assignee: H. B. Fuller Company, St. Paul, Minn.

[21] Appl. No.: 326,949

[22] Filed: Dec. 3, 1981

Related U.S. Application Data

[60] Continuation-in-part of Ser. No. 141,959, Apr. 21, 1980, abandoned, which is a division of Ser. No. 36,858, May 7, 1979, Pat. No. 4,259,220, which is a continuation-in-part of Ser. No. 944,845, Sep. 22, 1978, abandoned, and a continuation-in-part of Ser. No. 966,794, Dec. 6, 1978, abandoned.

[51] Int. Cl.[3] .................. B32B 27/08; B32B 31/08
[52] U.S. Cl. ............................... 428/517; 2/401; 156/164; 156/183; 156/229; 156/231; 156/244.11; 156/244.19; 156/244.22; 156/244.27; 156/269; 156/324; 156/334; 428/152; 428/906; 525/96; 525/98

[58] Field of Search ............... 156/84, 244.11, 164, 156/244.19, 183, 244.22, 205, 244.27, 229, 324, 231, 334, 269; 428/152, 517, 182, 906; 2/401; 128/284; 525/96, 98

[56] References Cited

U.S. PATENT DOCUMENTS

| | | | |
|---|---|---|---|
| 2,531,234 | 11/1950 | Seckel | 156/244.19 |
| 2,559,649 | 7/1951 | Little et al. | 156/231 |
| 3,600,250 | 8/1971 | Evans | 156/229 |
| 3,828,367 | 8/1974 | Bourgeois | 156/164 |
| 3,917,607 | 11/1975 | Crossland et al. | 525/99 |
| 3,932,328 | 1/1976 | Korpman | 525/98 |
| 3,976,530 | 8/1976 | Callan | 156/244.11 |
| 4,259,220 | 3/1981 | Bunnelle et al. | 525/98 |
| 4,300,967 | 11/1981 | Sigl | 156/164 |

*Primary Examiner*—John J. Gallagher
*Attorney, Agent, or Firm*—Merchant, Gould, Smith, Edell, Welter & Schmidt

[57] ABSTRACT

A self-adhering elastic comprises a block copolymer having glassy endblocks and an amorphous midblock, a midblock resin and an endblock resin.

21 Claims, 2 Drawing Figures

EXTRUDABLE SELF-ADHERING ELASTIC AND METHOD OF EMPLOYING SAME

This application is a continuation-in-part of Ser. No. 141,959, filed Apr. 21, 1980, now abandoned which is a division of Ser. No. 36,858 filed May 7, 1979 (now U.S. Pat. No. 4,259,220) which is a continuation-in-part of Ser. No. 944,845 filed Sept. 22, 1978 and Ser. No. 966,794 filed Dec. 6, 1978 (both abandoned).

Field of the Invention

The invention relates to elastic materials which are self-adhering imparting elastic properties to flexible nonelastic substrates.

BACKGROUND OF THE INVENTION

In the past, vulcanized rubber or synthetic rubber elastic bands or threads have been used to provide elastic properties to flexible substrates by attaching the elastic to the substrate using materials such as thread, yarn or adhesive in a sewing, weaving or adhesive process. The attachment of elastic bands to the underlying flexible substrate consumes additional materials and manufacturing overhead and poses substantial problems in the industry. Natural vulcanized or crosslinked synthetic rubbers are difficult to feed continuously and at high speeds in view of their tendency to stretch and relax during mechanical processes, resulting in articles with broken elastics, articles having an elastic with too great or too little tension or articles with partly attached elastics. Further, adhesives which have been used in the past to bond elastic bands to a flexible substrate generally have had poor adhesion to the elastic bands, resulting in the separation of the elastic during any substantial flexing of the substrate.

Buell, U.S. Pat. No. 4,081,301, issued Mar. 28, 1978, developed a process for attaching elastic leg bands to substrates, in which adhesive is applied along the length of continuous bands of elastic which are in a stretched condition, to a continuous web of substrate. The patent further suggests that the elastic can be coated with a heat-activated non-pressure sensitive adhesive prior to contact with the web. Still another suggestion relates to the use of a heat-sealable non-pressure sensitive elastic ribbon which can be adhered to the web with the aid of a suitable heating means.

Accordingly, a need exists for a self-adhering elastic band which can be continuously extruded and applied to flexible substrates at high speeds using automatic machines. A further need exists for a self-adhering elastic which during flex will resist detachment from the substrate. Another need exists for a self-adhering elastic having adequate tensile strength which can be attached with strong bonds to a flexible substrate at high machine speed without breaking.

Traditional elastic materials are generally crosslinked, three-dimensional networks of vulcanized natural or synthetic rubber. The crosslinked three-dimensional structure comprises a reversible energy storing network. Stress applied to the substance results in a strain or deformation of the three-dimensional network which stores energy, applied during stress, which can be spontaneously substantially recovered upon the removal of the stress. Elastic substances are ideal for imparting gathers to flexible substrates since they lengthen and contract in a constant and predictable manner through a wide temperature range.

Pressure sensitive adhesives, on the other hand, require a different set of properties. Upon the application of stress or force to a pressure sensitive adhesive, in the form of pressure, the adhesive must deform in order to come into intimate contact through viscous flow with the surface of a substrate in order to form adhesive bonds by Vander Walls attraction. Upon removal of the stress or pressure in order to preserve the adhesive bond, the adhesive must not recover from the deformation. Substances that are pressure-sensitive adhesives exhibit viscous flow and therefore inherently do not substantially recover from such deformation.

It is therefore apparent that elastic materials have minimal adhesive properties and pressure sensitive adhesives have minimal elastic properties. Commonly available pressure sensitive adhesive or elastic materials do not have the correct balance of properties which would result in a self-adhering elastic material since the molecular properties that result in elasticity are those that commonly result in the absence of adhesive properties. Only a unique combination of molecular properties can combine substantial elasticity and adhesive properties in a single composition.

See *Kirk-Othmer Encyclopedia of Chemical Technology*, 2nd Edition, John Wiley & Sons, Inc., New York, N.Y., 1963, Volume 1, pp. 371–404, and Volume 7, pp. 676–705 for a discussion of elastics and adhesives.

SUMMARY OF THE INVENTION

We have found certain block copolymer containing compositions having at least one midblock and at least two endblocks, having a narrow range of viscoelastic properties, which comprise a self-adhering elastic having a combination of elastic and adhesive properties. These block copolymer compositions have a reversible crosslink which, above a certain temperature, disappears permitting easy hot melt extrusion. Below this temperature the crosslinking can reappear creating elastic properties. These block copolymer compositions can be extruded above the endblock Tg temperature and attached to the substrate below the endblock Tg. As the material cools below the endblock Tg, the crosslinking again appears which provides elastic properties, substantially identical to natural vulcanized rubber and synthetic, crosslinked rubber. Linear block copolymers, having a block structure represented by the formulae:

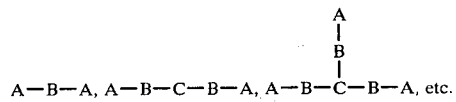

wherein B comprises a rubbery mid block, A comprises a glassy end block, and C comprises a coupling agent which can be used as the reversible crosslink graft copolymer.

A and B are thermodynamically incompatible one to the other and would separate into different phases if not chemically linked. The A end-blocks and the B midblocks attempt to achieve a lower energy level by repelling each other. At the same time similar A endblocks of neighboring molecules tend to attract each other forming hard glassy areas referred to as domains. These domains form a rigid three-dimentional structure throughout the composition resulting in elastic properties similar to vulcanized natural rubber or synthetic crosslinked rubber. The presence of the domains forming the three-dimensional structure results in the reversible crosslink property. As the temperature of the polymer is raised above the glass transition temperature (Tg) of the endblock polymer the domains are thermally disrupted and the three-dimensional network is destroyed. At this temperature the polymer will lose its elastic properties and can be easily extruded using hot melt type processes. However, after extrusion or application, as the copolymer cools to a temperature below the end-block Tg but above the midblock Tg, the domains reappear creating the crosslinked domain structure and elastic properties.

Coupling agents useful to make the linear or radial block copolymers can comprise a combination of an organometallic reagent and a di-, tri- or polyfunctional compound. The coupling agents are used in a coupling process which comprises reacting a block copolymer with an organometallic compound to form a metallic block copolymer compound which is in turn reacted with the di-, tri-, or polyfunctional compound producing either a linear, formed from a difunctional crosslinking agent, or a radial block copolymer having three radial arms (from a trifunctional compound), four radial arms (from a tetra-functional compound), etc. Examples of organometallic agents include n-butyl-sodium, n-butyl-lithium, etc. Examples of di-, tri-, or tetra-functional compounds include an alpha-omega-dihalo alkane, an alpha,alpha' dihaloxylene, a boron trihalide, a silicon tetra halide, etc. See Allport and Janes, *Block Copolymers*, pp. 76–88, John Wiley.

The self-adhering elastics of this invention typically require pressure to form a bond of appreciable strength. In other words, the tack is relatively non-aggressive but it will "cold flow" in the manner of most viscoelastic materials. Thus, self-adhering elastics of this invention have a rheology which permits a sufficient flow under pressure to form a strong adhesive bond while nevertheless maintaining a high level of cohesion, stretchiness, and elasticity.

An aspect of the invention relates to a self-adhering elastic suitable to provide elastic properties to flexible substrates. Another aspect of the invention relates to an article of commerce or a unit such as a garment or container which derives elastic properties from the presence of a strip of self-adhering elastic. Still another aspect of the invention relates to an elastic strip formed by the hot melt extrusion of the self-adhering elastic which is cut into an appropriate shape. Still another aspect of the invention is a roll of material which comprises the self-adhering elastic with a backing, which can be flexible or can have release characteristics, wound on a substantially circular form.

We have also found tackifying resins which can be added to elastic block copolymers to influence elasticity, adhesion and pressure sensitive tack properties to varying degrees. A first type, called midblock associating resins, are compatible with the rubbery midblock. These resins tend to increase the volume of the midblock fraction of the block copolymer, hence magnifying the rubbery adhesive nature of the midblock. The second type resin, called an endblock associating resin, is more compatible with the glassy endblock units than with the rubbery midblock. Endblock resins increase the volume fraction of the endblock, which tends to reinforce the three-dimensional domain network at the expense of viscous flow. In this way resins can be added to the block copolymer composition to balance the self-adhering properties and the elastic properties of the self-adhering elastics of the invention.

DEFINITIONS

"Hot melt" refers to thermoplastic solids with reasonably stable properties in the molten state, which are easily melted at modestly elevated temperatures (e.g. temperatures above 65° C.) and/or easily extruded, and which can be melted and resolidified a number of times without excessive degradation of the thermoplastic properties.

"Softening point" refers to a specific temperature or range of temperatures which can be determined by any of the standard softening point tests such as the ring and ball ("R & B") test. Accordingly, the term "softening point" includes and subsumes "softening range".

"Elastomer", "elastic", and "elastomeric" refer to a material which, in the form of an unsupported film or layer can be elongated to at least 100% of its original length and which will return with force to substantially its original length when permitted to contract spontaneously. Thus, this invention contemplates self-adhering elastics which would be defind as "elastomeric" by the American Society for Testing and Materials (A.S.T.M.). "Non-elastomeric" materials are those which exhibit significant deformation or "set" when elongated 100% of their original length or less; that is, such non-elastomeric materials typically do not provide the elongation-resistant forces or store the applied force.

"Essentially hydrocarbon resin" refers to a resin in the molecular weight range of a few hundred up to several thousand (e.g. 8,000) which is obtained or synthesized from rather basic hydrocarbons such as petroleum, coal tar, turpentine, olefins, etc. In the context of this invention, an "essentially hydrocarbon resin" need not be a hydrocarbon in the strictest sense of the term and may contain oxygen, nitrogen, sulfur, etc. Thus, an "essentially hydrocarbon resin" can be made from a monomer such as coumarone (also known as benzofuran). And, in industrial practice, coumaroneindene resins are typically referred to as "hydrocarbon resins".

The terms "loss tangent" (tan $\delta$ or $G''/G'$), and "storage modulus" ($G'$), are defined according to established principles of dynamic mechanics. These rheological quantities are measured on samples approximately 2.5 mm in thickness placed between 25 cm parallel plate fixtures of a Rheometrics Mechanical Spectrometer (RMS). The sample was allowed to equilibrate at the test temperature (e.g. 25° C. or 50° C.). A minicomputer governs the application of a 5% peak-to-peak shear strain to the sample. The frequency of the application can be controlled to a fraction of a Hertz (Hz). The values of the complex modulus ($G^*$) and loss tangent are calculated by the computer from geometry factors, peak-to-peak amplitude of the torque signal, and phase lag of the torque output wave. The definition of loss tangent and the relationship between $G^*$, $G'$, and $G''$ provide two equations in two unknowns which can be solved by the computer to provide $G''$ and $G'$, since $G^*$ and loss trangent are both known values calculated as described previously. For any of these values, the frequency in Hz (e.g. 0.25 Hz or 0.01 Hz) must be specified. Other instruments for measuring these rheological properties over a range of frequencies are known, e.g. the "RHEOVIBRON".

The term "dead load deformation" or "dead load creep" refers to a measurement of "cold flow" or permanent deformation at one or more fixed test temperatures, e.g. 23° C. or 25° C., 40 or 41° C., and 49 or 50° C. A sample of known length is suspended vertically in a chamber maintained at the test temperature and a mass is attached to the lower (free) end of the sample. The sample is cut to a size such that the force per unit area is 1500 g/cm$^2$. After approximately 3 hours at the test temperature, the sample is removed, the weight is detached, and the sample is allowed to relax under the influence of its own inherent elastomeric forces. The length of the relaxed sample ($L_2$) is compared to the original length ($L_1$) and the "dead load creep" (permanent deformation) is determined according to the formula $(L_2-L_1)/L_1 \times 100\%$.

DETAILED DESCRIPTION OF THE INVENTION

ELASTIC AND SELF-ADHERING PROPERTIES

HIgh elasticity and elastomeric behavior are manifested in a higher storage modulus (G'), and a lower loss tangent (tan δ or G''/G'), than is found in conventional pressure sensitive adhesives. However, the storage modulus values cannot preclude viscoelastic behavior in the temperature range of 25°–50° C. A self-adhering elastic with suitable "creep" or "cold flow" properties will have some tendency to flow in the temperature range of 25°–50° C., but this tendency should be kept within a limited range of loss modulus (G'') values.

The following are considered to be illustrative values for the G'', G', and tan δ (tan δ = G''/G') of a suitable self-adhering elastic.

| Property | Values in 10$^4$ dynes/cm$^2$ at 25–50° C. and 0.01–0.25 Hz |
|---|---|
| Loss Modulus (G'') | 5 to 100 |
| Storage Modulus (G') | 65 to 225 |
| Loss Tangent $\left(\tan \delta = \dfrac{G''}{G'}\right)$ | 0.03 to 1.0 (no units) |

Some frequency-dependence of these values can be observed, but extreme temperature dependence is not desirable. For example, a loss in modulus of more than $50 \times 10^4$ dynes/cm$^2$ in G' at 50° C., as compared to 35° C. indicates the likelihood of "heat set" or inadequate elastomeric behavior at moderately elevated temperatures. Permanent deformation due to elongation should not exceed about 1.5 times the original length of a sample of the self-adhering elastic (i.e. a permanent increase in length equal to 50% of the original length) throughout the 25°–50° C. range, using the dead load creep test described herein.

Viscoelastic extrudable self-adhering elastics of this invention preferably comprise a rubbery block copolymer, at least one endblock associating resin and at least one midblock associating resin. The resin which associates with the glassy end blocks of the block copolymer tends to increase the size of these crystalline domains decreasing the temperature dependence of the self-adhering elastic. The self-adhesive property of the elastic is believed to be dependent in part upon the high-viscosity liquid character of the elastic within the 25°–50° C. temperature range. A characteristic of a composition with viscous properties is that it will yield to stress, and at least some strain (in an oscillating stress situation) will be up to 90° out of phase with the stress. By contrast, in a perfectly elastic solid the stress and strain would always be in phase. The above ranges of G'', G', and loss tangent result in an effective balance of viscoelastic properties in the 25°–50° C. range, whereby at least a minimum amount of elasticity sufficient to result in elastic properties in inelastic materials is present (note the loss tangent <1 and the G' of $675 \times 10^4$ dynes/cm$^2$ or more), but in combination with some ability to flow or "wet out" a substrate (note the loss tangent >0.03, the G' $<200 \times 10^4$ dynes/cm$^2$, and G' $<100 \times 10^4$ dynes/cm$^2$), without resulting in a viscosity so low as to permit excessive "creep" or cold flow (note the G' $>5 \times 10^4$).

A tackifying resin with aliphatic character and relatively minimal aromatic character can associate with the midblock of the block copolymer and, if properly selected, help provide viscoelastic balance.

SELF-ADHERING ELASTIC

In view of the above discussion, a suitable self-adhering elastic will typically comprise:

(1) a block copolymer comprising at least one midblock B, and at least two endblocks A wherein B comprises a rubbery, or substantially amorphous polyolefin block, and A comprises a glassy vinyl arene block, (2) a mid-block associating resin, and (3) an essentially hydrocarbon, preferably aromatic, endblock associating resin having a Tg and a softening point above the Tg and softening point of the midblock associating resin and the end blocks of the block coolymer. Preferably the self-adhering elastic comprises:

(1) an effective amount of the block copolymer, (2) 20–150 parts of the mid-block associating resin, and (3) 5–150 parts of the end-block associating resin each per part of copolymer each per one hundred parts of the block copolymer.

The preferred elastics of this invention will have a ball and ring softening point within the range of 65° to 240° C., and will exhibit elastomeric behavior above the midblock glass transition temperature for extended periods at body temperature (e.g. 37° C.).

BLOCK COPOLYMERS

A number of rubbery block copolymers can be used to produce the self-adhering elastic compositions of this invention, as can be seen from the disclosures in U.S. Pat. Nos. 3,686,107, 3,736,281, 3,827,999, 3,935,338, 3,954,692, and 4,089,824. Additional disclosures of this type can be found in British Pat. No. 1,405,786 and trade literature of Phillips Petroleum Company and Shell Chemical Company. The block copolymers used in this invention have a three-dimensional crosslinked structure below the end-block Tg and are elastomeric. The copolymers are also thermoplastic in the sense that they can be melted above the end-block Tg, formed, and resolidified several times with little or no change in physical properties (assuming a minimum of oxidative degradation).

One way of synthesizing such rubbery block copolymers is to polymerize the vinyl arene glassy end-blocks separately from from the rubbery mid-blocks. Once the mid- and end-blocks have been separately formed, they can be linked. Typically midblocks can be obtained by polymerizing di- and tri-unsaturated $C_4$–$C_{10}$ hydrocarbons, e.g. dienes such as butadiene, isoprene, etc. and trienes such as 1, 3, 5 heptatriene, etc. When an endblock A is joined to mid-block B, an A-B block copolymer unit is formed, which unit can be coupled by various techniques or with various coupling agents (C) to provide a structure such as A-B-A, which is believed to comprise two A-B blocks joined together in a tail-to-tail A-B-C-B-A arrangement. By a similar technique, a radial block copolymer can be formed having the formula $(A-B)_nC$, wherein C is the hub or central, polyfunctional coupling agent and n is a number greater than 2. Using the coupling agent technique, the functionality of C determines the number of A-B branches.

Block A comprises a poly(vinylarene) having an average molecular weight between 1,000 and 60,000, and block B comprises a substantially amorphous polyolefin such as polyisoprene, ethylene-propylene polymers, polybutadiene, etc. having an average molecular weight between 5,000 and 450,000. The total molecular weight of the block copolymer is preferably about 100,000 to 400,000, most preferably about 200,000–300,000. An extensive discussion of rubbery radial block copolymers can be found in the disclosure of the aforementioned U.S. Pat. No. 4,089,824. The residual unsaturation in the midblock or diene-containing portion of the block copolymer molecule can be hydrogenated selectively so that the content of olefinic double bonds in the radial block copolymers can be reduced to a residual proportion of less than 5% or even less than 2%. Such hydrogenation tends to reduce sensitivity to oxidative degradation and may have beneficial effects upon elastomeric properties.

Preferred block copolymers used in this invention comprise at least two substantially polystyrene end block and at least one substantially polyisoprene midblock. Isoprene typically comprises the major amount of the repeating units in the block copolymer and can constitute, for example, 70% by weight or more of the block copolymer molecule. The polymer, if radial, can have three or more arms, and good results can be obtained with, for example, four, five, or six arms. The midblock can be hydrogenated, if desired.

Linear or A-B-A type block copolymers (including A-B-A-B-A, etc.) are preferably selected on the basis of end block content, large end blocks being preferred. For S-I-S (polystyrene-polyisoprene-polystyrene) block copolymers, a styrene content in excess of 14% by weight is preferred, e.g. 15–30% by weight. A commercially available example of such a linear polymer is KRATON® 1111 rubber, an S-I-S polymer which contains about 21.5% styrene units, essentially the balance being isoprene units. Thus, the optimum styrene content for linear S-I-S copolymers appears to be greater than 20% by weight. As a result of the higher styrene content, the polystyrene end blocks have a relatively high molecular weight. Typical properties of KRATON® 1111 are reported to include a tensile strength of 2900 psi ($2.0 \times 10^6$ Kg/m$^2$), a 300% modulus of 200 psi ($1.4 \times 10^5$ Kg/m$^2$), an elongation of 1200% at break, a 10% set at break, and a Shore A hardness of 52; the Brookfield viscosity of a toluene solution is 1300 centipoise at room temperature, less than that of KRATON® 1107.

MIDBLOCK RESINS

A variety of resins with tackifying properties are compatible with polymerized diene polymer midblocks, including those diene blocks which have been hydrogenated so as to become virtually identical, chemically and physically, to polymerized mono-olefins (e.g. polyethylene, polypropylene, polybutylene, etc.). These midblock associating resins tend to associate with the rubbery midblock of the linear or radial block copolymer and thereby tend to extend or build up as well as tackify these rubbery midblocks. Both natural and synthetic essentially hydrocarbon resins can be used as midblock associating resins, provided that these resins contain substantial aliphatic character, which character can be provided by the aliphatic portion of rosin acids, repeating isoprene or other diene units (e.g. polymerized 1,3-pentadiene), polymerized cycloaliphatics, and the like.

Although esters of polyhydric alcohols and rosin acids will associate with a rubbery midblock, some of these esters tend to detract from the elastic recovery characteristics of the self-adhering elastic and are not preferred. Essentially hydrocarbon resins are preferred, particularly the so-called "terpene" resins, i.e. polymers with repeating $C_5H_8$ or $C_{10}H_{16}$ units. These polymers can be natural or synthetic and can be copolymers (including terpolymers, etc.), since isoprene is an olefin which can be copolymerized with other olefins.

All terpene resins do not work with equal effectiveness in this invention, and synthetic terpenes having a softening point (ball and ring method) of about 80° to about 115° C. are preferred, particularly the commercially available resin known as "WINGTACK" 95. This commercially available terpene resin is reported to be derived from a mixed olefin feedstock as a by-product of isoprene or polyisoprene production. According to U.S. Pat. No. 3,935,338 and South African Pat. No. 700,881, "WINGTACK" 95 (trademark of Goodyear Tire and Rubber Company) is a thermoplastic tackifying resin essentially comprising a copolymer of piperylene, 10% isoprene, 5% cyclopentadiene, 15% 2-methyl-butene, and about 10% dimer. Other tackifying resins of the same general type typically comprise 20–80 weight-% of piperylene and 80–20 weight-% of 2-methyl-butene.

Good elastic memory or elastic recovery characteristics can be obtained with natural hydrocarbon resins such as "PICCOLYTE D-135" (trademark), a natural dipentene terpene resin. However, this resin is not as effective as the "WINGTACK" 95 in providing good adhesive properties, e.g. good PSTC-1 peel.

The naturally occurring terpenes can be classified as monocyclic (dipentene), dicyclic (pinene), or acyclic (micrene). A small amount of cyclic character is not detrimental in the context of this invention. A significant amount of aromatic character in the terpene resin is, however, ordinarily avoided, if such aromatic character is sufficient to interfere with the midblock associating properties of the resin.

END BLOCK RESINS

As explained in British Pat. No. 1,405,786, resins with aromatic character tend to associate with the vinyl arene end blocks. Such end block resins include the coumarone-indenes, polystyrene, poly-alpha-methylstyrene, the polyindenes, and other resins containing mono or polycyclic aromatic groups. Such resins are commercially available, e.g. "KRISTALEX", "PICCOTEX 75" (a low molecular weight alpha-methylstyrene-vinyl toluene synthetic copolymer), "PICCOTEX 100" (trademark for higher molecular weight version of "PICCOTEX 75), "PICCOLASTIC D-150" (trademark for polystyrene resin), and the "CUMAR" resins (trademark for coumarone-indenes). It is particularly desirable that the end block associating resin have a glass transition temperature (Tg) and a softening point above those of the end block and of the midblock associating resin. For example, it would ordinarily not be desirable for the glass transition and for significant heat softening to occur below about 80°–110° C.; hence, end block resins with somewhat higher molecular weights and softening points above 115° C. are typically selected. From the standpoint of strong elastic recovery (both initial and aged) and good adhesive properties, high softening point, either an alpha-methyl styrene or a coumaroneindene resin is preferred. Preferred resins with softening points within the range of 140°–160° C. are commercially available.

VISCOELASTIC PROPERTIES

The adhesive bond strength of self-adhering elastic can be measured by 180° peel resistance tests such as PSTC-1. The adhesive tack can be measured, for example, by probe tack tests such as A.S.T.M. D2979. Cohesion and stretchiness of adhesives can be measured with modern tensile testing equipment.

Considerable skill and knowledge already exist in the adhesive art with respect to determining proportions of tackifiers and rubbery block copolymers. Probe tack values and initial (immediate) PSTC-1 values have been found to be unreliable or unreproducible indicators of self-adhering or elastic performance in the context of this invention while PSTC-1 values, taken 24 hours after the adhesive bond has been formed, "dead load deformation" ("creep"), and the rheological properties (G', G'', loss tangent), described previously have been found to be reliable, reproducible parameters of elastomeric behavior.

Preferred PSTC-1 values, determined 24 hours after formation of the bond between a substrate and the self-adhering elastic, at room temperature on the standard steel plate using pressure from the standard 2 Kg roller values in excess of 1 pound per inch width (1 p.i.w.), i.e. wherein more than 450 grams at 180° peel force is needed to delaminate a tape/steel plate sample wherein the tape sample is 25.4 mm in width. PSTC-1 values in excess of 1500 g/25.4 mm-sample or even 3000 g/25.4 mm-sample can be obtained in practice. These values are believed to indicate a reasonably permanent or semi-permanent bond between the self-adhering elastic of this invention and a polymeric film substrate of the type used in articles of clothing including disposable diapers. The ring and ball softening point of the elastic is about 65° to 240° C.

Tensile strength values for the elastic of this invention at 20°–25° C. can be determined as a measure of cohesive strength. Values in excess of $3 \times 10^4$ Kg/m² (e.g. above 33,000 Kg/m²) can be obtained in practice. At 20°–250° C. and 500% elongation the tensile strength should be at least 50 pounds per square inch.

Dead load deformation values $$\left( \frac{L_2 L_1}{L_1} \times 100\% \right)$$

(1500 g/cm² for 3 hours at the test temperature) can be well below 100% and even below 50% throughout the range of 25° C. to 50° C., as compared to the room temperature value.

Preferred and optimum rheological parameters are set forth below.

TABLE OF PREFERRED AND OPTIMUM RHEOLOGICAL PROPERTIES
(All values in $10^4$ dynes/cm² for G'' and G')

| Property | PREFERRED (at 25–50° C.) | | OPTIMUM (at 25–50° C.) | |
|---|---|---|---|---|
| | at 0.01 Hz | at 0.25 Hz | at 0.01 Hz | at 0.25 Hz |
| Loss Modulus (G'') | 5–25 | 10–100 | 8–16 | 15–35 |
| Storage Modulus (G') | 75–200 | 75–200 | 100–175 | 120–200 |
| Loss Tangent (tan δ) | 0.05–0.3 | 0.08–1.0 | 0.07–0.10 | 0.01–0.25 |

Specific Embodiments

With these physical properties in mind, proportions of block copolymer, endblock and midblock resins can be selected to provide an effective self-adhering elastic with good elastic recovery or elastic memory characteristics. The following Table of broad, preferred, and optimum proportions assumes that the rubbery block copolymer is either (1) "SOLPRENE ® 418", trademark of Phillips Chemical Company for a radial isoprene-styrene block copolymer having an approximate molecular weight of 300,000, a specific gravity of 0.92, an inherent viscosity in toluene of 1.16, and an isoprene/styrene ratio of 85/15, or (2) KRATON ® 1111, trademark of Shell Chemical Co. for a polystyrene-polyisoprenepolystyrene (S-I-S) block copolymer containing 21.5% styrene, the balance being isoprene. This copolymer has the previously reported tensile strength, 300% modulus, elongation at break, set at break, and Shore A hardness. The Brookfield viscosity in toluene is 1300 cps. SOLPRENE ® 418 in toluene has a viscosity of 2,900 centipoise at 25° C. Hydrogenated linear block copolymers, including those of the styrene-isoprene-styrene type are available according to U.S. Pat. No. 3,827,999; see also U.S. Pat. No. 4,089,824, which discloses the hydrogenated butadiene analog. Such hydrogenated block coolymers can be used in the context of this invention. Compounds of the "KRATON ® G" series (trademark of Shell Chemical Company) have a saturated or essentially saturated ethylene-butylene midblock and, if used, are preferably used in combination with the KRATON ® 1111 or SOLPRENE ® 418 type of rubbery copolymer.

The aforemetioned Table of proportions is set forth below.

TABLE OF PROPORTIONS FOR BLOCK COPOLYMER AND RESINS

| Ingredient | Amount | | |
|---|---|---|---|
| | Broad Parts by Weight | Preferred Parts by Weight | Optimum Parts by Weight |
| Rubbery block copolymer | 100 | 100 | 100 |
| Midblock resin | 20–150 | 40–100 | 72.5–77.5 |
| End block resin | 5–150 | 30–100 | 45–55 |

(NOTE: wt % = percentage by weight of total self-adhering elastic.)

The most effective criteria for the selection of amounts and types of ingredients are believed to be (a) rheological properties such as G', G'', loss tangent, and (b) dead load creep test results. New resins and new block copolymers are constantly being discovered, and the formulation of suitable elastics can be attempted with new materials by referring to these criteria.

The self-adhering elastic of this invention can be used to impart elastic properties to substantially inelastic substrates in a variety of ways. The elastic can be extruded and directly contacted with the substrate at ambient (about 25°-30° C.) to elevated temperature (above the endblock Tg). In this way close-fitting garments which need a small amount of elastic property can derive the property from the self-adhering elastic. The elastic can be extruded and contacted either at ambient or at an elevated temperature with a substrate that is pre-gathered. In articles such as garments which need a large amount of elastic stretch, the self-adhering elastic composition can be bonded to exterior portions of gathers formed from the material, permitting the gathered material to be stretched greatly, the elastic providing a force returning the article to its original gathered state. The elastic can conveniently be attached by contacting the elastic to the substrate and cooling the elastic simultaneously. Another way to impart elastic gathers to the substrate comprises extruding the elastic, cooling the elastic to below the endblock (Tg), at which point the elastic properties arise, stretching (placing the band under tension) the elastic and contacting the elastic to bond to the substrate. Once the bond has formed, the tension can be released and the substrate is gathered by the force of the contraction of the elastic. Clearly these methods are preferably performed with machines that extrude and contact the elastic continuously and at high speed.

The self-adhering elastic of the invention can be extruded and stored in the form of a roll which comprises the band of elastic wound on a substantially circular form. The elastic on the roll can have a continuous backing made from a flexible, elastomeric or non-elastomeric backing, preferably having release properties, which is attached to the elastic band in a way that it can be detached or released from the roll. The elastic an also be coated with a composition having release characteristics. The elastic band can easily and rapidly be manufactured by coextruding the elastic with the backing.

The self-adhering elastics can be attached to substrates such as woven or nonwoven materials. Woven materials include fabrics made from synthetic or natural fibers including polyester cotton, wool, paper, graphite, nylon, etc. Nonwoven material include sheets made from polyethylene, polyester, nylon, paper, etc. The subtrates can be substantially inelastic or can have some elastic properties which are reinforced, supported, or strengthened by the self-adhering elastic of this invention.

The band can also be "indexed" with a moving web to provide a series of discrete circular or eliptical bands. Such "indexed" bands can provide a hat-banding effect (e.g. for mass-produce surgical caps), a gathered, banded opening for a plastic bag, a waist band, or the like. In the case of disposable diapers, however, it is not necessary for the band to form a complete circle; the essential equivalent of a circular leg band results when the diaper is joined together at the child's hips.

In addition to the block copolymer and resins, the self-adhering elastic of this invention can contain common compatible antioxidants, stabilizers, or additives which do not reduce the elastic or self-adhesive properties of the combination of the rubbery block copolymer and the resins but provide other useful properties. For example, minor amounts of fillers and pigments can be included in the elastic typically in amounts comprising about 0.001 to 20 parts by weight per 100 parts of the block copolymer of the self-adhering elastic composition. Substantially inert extenders can also be included in the composition, e.g. the typical hydrocarbon process oils in an amount which does not substantially reduce elasticity or adhesion which commonly comprises less than 25 weight-% of the composition, since larger amounts of oil will detract from the elastic characteristics of the self-adhering elastic.

Typical antioxidants useful in self-adhering elastics of this invention include a pentaerithritol phosphite ester (e.g. di[stearyl] pentaerithritol diphosphite), a hindered phenol or polyphenol, etc. Typical hindered phenol-type antioxidants include those in which a phenolic (i.e. hydroxyphenyl or hydroxybenzyl) group or groups is or are substituted on a short hydrocarbon chain, and the hydroxy group of the phenolic substituents is hindered by nearby or adjacent alkyl groups substituted on the phenol nucleus. Such structures can be obtained, for example, by alkylating, Typical pigments useful in formulating self-adhering elastics of this invention include titanium dioxide, typically having a particle size in the sub-micrometer range, and similar finely divided materials. Fillers may tend to be a bit coarser in particle size, though still typically smaller than 40 uM (minus 325 U.S. mesh), e.g. finely ground calcium salts or silicates.

The following materials can be used to prepare the self-adhering elastic of the invention:

"SOLPRENE® 418": trademark for the radial block copolymer described previously.

"SOLPRENE® 423": another trademark for essentially the same radial block copolymer in a pellet form.

"KRATON® 1111": trademark of Shell Chemical Co. for the polystyrene-polyisoprene-polystyrene copolymer described previously.

"KRATON® 1107": trademark of Shell Chemical Co. for polystyrene-polyisoprene-polystyrene linear block copolymer having a styrene/isoprene ratio of 14/86.

"WINGTACK 95": trademark for synthetic polyterpene resin described previously.

"KRISTALEX® 3100": trademark of Hercules Inc. for low molecular weight thermoplastic hydrocarbon resin of the alpha-methylstyrene type having a ring and ball softening point of 97°-103° C., an acid number less than 1.0, a bromine number which is typically about 2, a specific gravity at 25° C. of 1.06, and a melt viscosity of 10,000 centipoise (cps) at 128° C., 1,000 cps at 152° C., and 100 cps at 190° C. The softening point substantially below 115° C. (typically not more than 103° C.) indicates a spectrum of molecular weights, with a significant number of resin molecules having molecular weights well below those of the relatively pure, narrow-spectrum coumarone-indene resins which are commercially available, e.g. as the "CUMAR" (trademark) series described subsequently. (It has been found that the higher molecular weight, higher softening point, narrow-spectrum aromatic hydrocarbon resins are preferred for use as "endblock" association with the rubbery block copolymers described previously.)

"CUMAR LX-509": trademark of Neville Chemical Company for coumarone-indene resin having a softening point (by the ring and ball technique of A.S.T.M. E-28) of at least about 155° C., a specific gravity at 25/15.6° C. of 1.114, and an average molecular weight (by osmometry) of 1,120.

"EASTMAN ® Resin H-100": trademark of Eastman Kodak Company for a hydrocarbon resin produced from petroleum feedstock by polymerization, followed by hydrogenation. This particular hydrocarbon resin has an acid number less than 0.1, a density at 23° C. of 1.04 g/cm$^3$, a Brookfield viscosity at 190° C. of 200 centipoise, a bromine number of 11.1, and a ring and ball softening point (A.S.T.M. E-28) which is reported to be 100° C. and in any event is below 115° C.

"IRGANOX 1010": trademark of Ciba-Geigy for an antioxidant and thermostabilizer of the hindered phenol type.

"SOLPRENE ® 420": trademark for a branched, teleblock copolymer having polystyrene terminal blocks and a structure essentially similar to "SOLPRENE ® 423", except for a lower molecular wegit.

"KRATON ® 1102": trademark for S-B-S (styrene-butadiene-styrene) block copolymer having a styrene/butadiene ratio of 28/72, a Brookfield viscosity in toluene solution (25 weight-%) of 1200 centipoise at 25° C., a specific gravity of 0.94, a Shore A hardness of 62, a set at break of 10%, an elongation of 880% (A.S.T.M. method D412 with a tensile tester jaw separation speed of 25.4 cm/min.), a 300% modulus of 281,200 Kg/m$^2$, and a tensile strength (same A.S.T.M. method as the elongation determination) of $3.23 \times 10^6$ Kg/m$^2$ determined on typical films cast from a toluene solution.

"WESTON ® 618": trademark of Borg Warner Corporation for an antioxidant described in U.S. Pat. Nos. 3,047,608 and 3,205,269, i.e. an antioxidant which is reported to be di(stearyl) pentaerythritol diphosphite.

For convenience of sample preparation, the antioxidants and pigments were sometimes omitted from the exemplary formulations which follow. Since incompatibility between resins and various portions of the rubbery block copolymer tend to be minimized in the molten state, the order of addition of ingredients is not usually critical. It is generally preferred to begin with one of the relatively larger components such as the rubbery block copolymer and add the tackifiers and other resins to it, e.g. adding the synthetic terpene midblock associating resin next, followed by the endblock associating resin. Samples can be prepared by blending in a solvent medium; however, the data obtained from such samples is believed to be less reliable as compared to samples formulated in the molten state. Samples can be solvent-cast to films ranging from 100 to 200 micrometers for test purposes, even though the industrial practice of this invention involves extrusion of the hot melt self-adhering elastic.

DESCRIPTION OF THE DRAWINGS

Turning now to the Drawing, FIG. 1 illustrates the use of a pre-tensioned, cooled band of self-adhering elastic to bond two continuous substrates, which can have a thickness of less than 5 mm and preferably less than 0.5 mm, into an assembly having gathers all along the bond line. A hot melt reservoir 11 extrudes an elongated extrudate (referred to herein as a "band") by forcing the self-adhering elastic material in reservoir 11 through an extrusion die 12. The band 13 comes into contact with chill rolls 15 and 16 almost immediately after the extrusion step, so that band 13 wil be cooled to a temperature below its softening point, e.g. to a normal ambient temperature such as 20°–25° C. (Typically, the self-adhering elastic will be formulated to have a midblock glass transition temperature below normal ambient temperatures). Chill rolls 15 and 16, in addition to cooling band 13, also advance it toward tensioning rolls 17 and 18. Accordingly, the portions 23 and 33 of band 13 which are on either side of tensioning rolls 17 and 18 will be under tension and will be in an essentially elongated state. Tensioning rolls 17 and 18 advance portion 33 of band 13 to nip rolls 27 and 28. Substrates 22 and 32 are all the while being continuously unreeled from storage rolls 21 and 31, so that the pretensioned, cooled band of self-adhering elastic 33 and substrates 22 and 32 all enter the nip provided by rolls 27 and 28 to be formed into the composite or assembled product 40 (i.e. the banded substrates). Although nip rolls 27 and 28 can be heated to a moderately elevated temperature, in the preferred embodiment of this invention, the modest pressure provided by the nip rolls is all that is needed to adhesively bond substrate 22 to substrate 32 with the self-adhering elastic band 33. Since the nip rolls 27 and 28 provide only line contact with the composite or assembly comprising substrate 22 and 32 and adhesive 33, it is difficult to express the pressure applied by these rolls in conventional terms such as Kg/m$^2$ or the like. Light pressure on the order of tens or hundreds of grams per square centimeter can be sufficient; however, there is almost no upper limit on the pressure applied by nip rolls 27 and 28 so long as the rolls themselves or the substrates 22 and 32 are not damaged. The self-adhering elastic in band 13 can be formulated to take into account the amount of pressure available at nip rolls 27 and 28.

Figure 1:
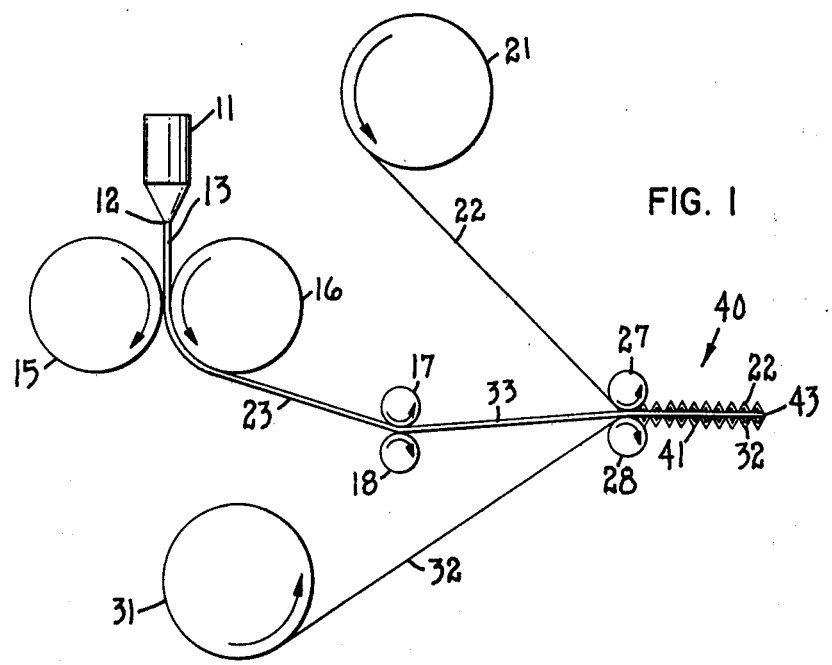
FIG. 1 is a schematic illustration of a typical apparatus and typical method steps used in a preferred embodiment of this invention.

Since band 13 is a self-adhering elastic which meets the definition of an elastomer, it will tend to contract spontaneously with force if the tension applied to banded substrates 40 is less than the tension on portion 33 of band 13. For example, additional rolls or conveying devices (not shown) can be used on banded substrates 40 merely to move the composite product along toward a cutting station and not exert any significant tension upon the banded substrates. In such a situation, the portion 43 of band 13 on the exit side of nip rolls 27 and 28 will spontaneously cause the formation of gathers 41 all along the line of the adhesive bond between portion 43 of band 13 and substrates 22 and 32.

The banded substrate product 40 can be cut into individual elastic-banded articles such as disposable diapers by techniques known in the art.

Figure 2:
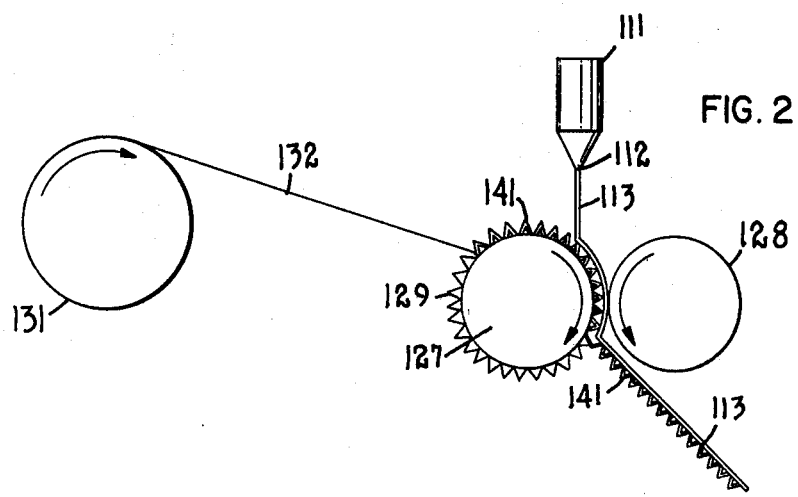
FIG. 2 is a similar schematic illustration of another embodiment of this invention.

In the embodiment of the invention shown in FIG. 2, pre-tensioning of the hot melt self-adhering elastic band 113 is not required. As in FIG. 1, band 113 is extruded from reservoir 111 through extrusion die 112. A single substrate 132 is continuously unreeled from storage roll 131. Substrate 132 is taken up by vacuum chill roll 127 at a point which permits pre-gathering of the substrate. Teeth-like projections 129 on the surface of vacuum chill roll 127 create the flutes or gathers 141 in substrate 132. The two chill rolls 127 and 128 serve to cool band 113 in a manner analogous to the action of chill rolls 15 and 16 of FIG. 1; in addition, these chill rolls apply light pressure to the composite of the band 113 and the pre-gathered substrate 132, so that the pressure-sensitive adhesive bond between band 113 and substrate 132 is formed without permanently flattening out gathers 141. This result occurs because, in the composite emerging from the exit side of rolls 127 and 128, band 113 tends to be bonded only to the peaks of gathers 141.

COMPARATIVE PREPARATION A

The following ingredients were blended in a heated mixer in the indicated amounts.

| Wt.-% | Ingredient |
|---|---|
| 65.4 | Radial isoprene-styrene elastomeric block block copolymer (SOLPRENE ® 423). |
| 32.7 | High softening-point, high molecular weight coumarone-indene resin (CUMAR ® LX-509). |
| 0.2 | Phosphite ester antioxidant (WESTON ® 618). |
| 0.2 | Hindered phenol antioxidant ("IRGANOX" 1010). |
| 1.5 | Titanium dioxide pigment (rutile, alumina-treated). |

A purpose of this Example was to evaluate the effect upon rheology and room-temperature 180° peel strength when the radial block copolymer/resin blend was provided with large glassy (vinyl arene) domains and minimally tackified or plasticized rubbery (elastomeric) domains, in this case no "midblock" resin. According to the scientific and patent literature, the coumarone-indene resin will associate with the polystyrene end blocks of the radial elastomeric block copolymer.

COMPARATIVE PREPARATION B

The following formula is a rubbery block copolymer/tackifier resin blend which would have low tack and peel and would have significant elastomeric behavior at normal ambient temperatures. The formula theoretically contains no "endblock" resin.

| Wt-% | Ingredient |
|---|---|
| 50 | Linear S-B-S (polystyrene-polybutadiene-polystyrene) elastomeric block copolymer (KRATON ® 1102). |
| 35 | Hydrocarbon resin (EASTMAN ® Resin H-1000). |
| 15 | Staybelite Ester 10 (HERCULES ® glycerol ester of hydrogenated rosin, 83° C. softening point). |

COMPARATIVE PREPARATION C

This formula was similar to that of Example B, except that an S-I- (polystyrene-polyisoprene-) radial block copolymer was blended with a different tackifier.

| Wt-% | Ingredient |
|---|---|
| 50 | Radial S-I- elastomeric block copolymer (SOLPRENE ® 418). |
| 50 | Polyterpene resin (WINGTACK ® 95). |

COMPARATIVE PREPARATION D

This formula had both "endblock" resin and "midblock" resin in addition to the S-I-S block copolymer; however, more than 80% by weight of the "endblock" resin was a relatively low molecular weight, low softening point material. The block copolymer was also a relatively lower molecular weight material. Room temperature performance of the formula would be expected to include poor self-adhering properties and some elastomeric behavior, but at higher temperatures (e.g. 37° C.), performance would be unpredictable.

| Wt-% | Ingredient |
|---|---|
| 40.0 | Low molecular weight, radial, elastomeric block copolymer (SOLPRENE ® 420). |
| 0.1 | Phosphite ester antioxidant (WESTON ® 618). |
| 0.1 | Hindered phenol antioxidant ("IRGANOX" 1010). |
| 1.0 | Titanium dioxide pigment (rutile, alumina-treated). |
| 32.8 | Hydrocarbon resin (EASTMAN ® Resin H-100). |
| 4.0 | High molecular weight coumarone-indene (CUMAR ® LX-509). |
| 22.0 | Alpha-methylstyrene resin (typical softening point: 100° C.) ("Kristalex" 3100 [trademark]). |

COMPARATIVE PREPARATION E

This formula appeared to conform to all of the criteria of a formula of this invention, except that the amount of "endblock" resin was relatively high and the amount of polyterpene tackifier was relatively low.

| Wt-% | Ingredient |
|---|---|
| 45.0 | High molecular weight, radial S-I- elastomeric block copolymer (SOLPRENE ® 418). |
| 15.0 | Polyterpene resin (WINGTACK ® 95). |
| 40.0 | High molecular weight, high softening point coumarone-indene (CUMAR ® LX-509). |

EXAMPLES I–V

The formulas for Examples I through V are set forth in the following Table.

| | INGREDIENTS IN WEIGHT-% | | | | |
|---|---|---|---|---|---|
| Example | S-I-S Linear Block Copolymer | S-I Radial Block Copolymer | Polyterpene Resin (WINGTACK ® 95) | Coumarone-indene (CUMAR ® LX-509) | Miscellaneous[1] |
| I | 43.6[2] | — | 32.7 | 21.8 | 1.9 |
| II | 43.6[3] | — | 32.7 | 21.8 | 1.9 |
| III | — | 43.6[4] | 32.7 | 21.8 | 1.9 |
| IV | 39.6[3] | — | 32.4 | 26.1 | 1.9 |
| V | — | 38.0[5] | 45.0 | 17.0 | — |

NOTES
[1] This "miscellaneous" component consisted of 0.2% WESTON ® 618, 012% "IRGANOX" 1010, and 1.5% titanium dioxide pigment (rutile, alumina-treated).
[2] KRATON ® 1111, described previously.
[3] KRATON ® 1107, described previously.
[4] SOLPRENE ® 423, described previously.
[5] SOLPRENE ® 418, described previously.

RHEOLOGICAL TESTING

The G", G', loss tangent (G"/G') were determined, as described previously, at 25° and 50° C. and at 0.01 and 0.25 Hz. The results for the Comparative Preparations and Examples 1-5 are set forth below. All G" and G' data are in $10^4$ dynes/cm$^2$. For purposes of comparison, typical data for vulcanized natural rubber (at 0.5 Hz) are included.

TABLE I

| | Frequency: 0.01 Hz Temperature: 25° C. and 50° C. | | | | | |
|---|---|---|---|---|---|---|
| | G" | | G' | | loss tan | |
| Comparative | 25° | 50° | 25° | 50° | 25° | 50° |
| Preparation | | | | | | |
| A | 121 | 140 | 89.5 | 323 | 1.351 | .428 |
| B | 16.6 | 21.7 | 129 | 74.5 | .129 | .290 |
| C | 4.65 | 6.16 | 67.4 | 71.7 | .069 | .086 |
| D | 53.3 | 22.7 | 173 | 65.3 | .308 | .408 |
| E | 20.2 | 21.9 | 345 | 336 | .058 | .065 |
| Example | | | | | | |
| I | 12.8 | 9.28 | 128 | 131 | .100 | .071 |
| II | 13.6 | 12.4 | 146 | 151 | .093 | .082 |
| III | 14.2 | 15.6 | 161 | 163 | .088 | .096 |
| IV | 11.4 | 10.1 | 130 | 123 | .087 | .082 |
| V | 13.3 | 5.23 | 69.7 | 64.9 | .191 | .081 |

TABLE II

| | Frequency: 0.25 Hz Temperature: 25° C. and 50° C. | | | | | |
|---|---|---|---|---|---|---|
| | G" | | G' | | loss tan | |
| Comparative | 25° | 50° | 25° | 50° | 25° | 50° |
| Preparation | | | | | | |
| A | 180 | 173 | 148 | 323 | 1.215 | .440 |
| B | 31.5 | 19.3 | 171 | 110 | .187 | .173 |
| C | 15.0 | 5.48 | 78.9 | 82.3 | .190 | .067 |
| D | 138 | 45.7 | 311 | 130 | .442 | .351 |
| E | 34.3 | 23.0 | 386 | 372 | .089 | .062 |
| Example | | | | | | |
| I | 33.1 | 15.5 | 164 | 152 | .203 | .102 |
| II | 25.7 | 15.6 | 175 | 176 | .147 | .089 |
| III | 32.1 | 18.1 | 197 | 190 | .163 | .096 |
| IV | 31.3 | 15.1 | 167 | 145 | .188 | .104 |
| V | 73.3 | 9.68 | 115 | 76.4 | .639 | .127 |
| Natural Rubber (estimated) | 40 | 40 | 800 | 800 | .05 | .05 |

For Preparation A, the high G' values and the temperature dependency of these values indicate that the composition cannot be easily attached to a substrate since the high G' indicates good elastic behavior, but poor adhesive performance. The rheological parameters were comfirmed by 180° peel data (PSTC-1). Even 24 hours after formation of the elastic to substrate bond, no PSTC-1 value could be obtained. "Dead load deformation" values were acceptable, ranging from 0% to only 67% throughout the 25°-50° C. range.

For Preparation B, the temperature dependence of G' also indicates the strength of the bond between the elastic and the substrate is temperature dependent and will fail at elevated temperature, which is reflected in the "dead load deformation" data. These data were as follows: 20% at room temperature, 344% at 37.8° C., and 528% at 43.3° C. Cohesive failure occurred at 48.9° C.

For Preparation C, G" at 0.01 Hz (25° C.) was marginal, and at 0.25 Hz (50° C.) was very low; G' data at 0.01 Hz were marginal. This analysis of the rheological parameters was confirmed by "dead load deformation" data: 6% at room temperature, 44% at 37.8° C., 92% at 43.3° C., and cohesive failure at 48.9° C. The PSTC-1 values after 24 hours were acceptable (2770 g/25.4 mm-width), indicating the ability to wet out a substrate (but inadequate resistance to heat set).

Preparation D did not form an adequate bond to the substrate and performed poorly in the "dead load deformation" test. It is believed that the high G" and, most important, temperature dependence of G' were significant in these regards.

The high coumarone-indene content of Preparation E was believed to be reflected in the high G' values. The bond of Example E to the substrate was reliable (e.g. 910 g/25.4 mm-width in PSTC-1), but a sample of Preparation E performed adequately in the "dead load deformation" test.

Examples I-IV performed well in terms of both (1) PSTC-1 (180° peel) values taken at room temperature 24 hours after the bond between the elastic and the substrate formed and (2) "dead load deformation". Example 5 showed excellent PSTC-1 performance but nearly failed the "dead load defomation" test. The 24-hour PSTC-1 values for Examples I, III, IV, and V are set forth below. All samples tested were 25.4 mm in width, and the values are reported in grams per 25.4 mm-width.

| Example I | 2670 g/25.4 mm |
| Example III | 2170 g/25.4 mm |
| Example IV | 2130 g/25.4 mm |
| Example V | 3580 g/25.4 mm* |

*determined immediately rather than after 24 hours. PSTC-1 values above 4500 g/25.4 mm or even 4000 g/25.4 mm are difficult to obtain in practice without sacrificing other desired properties.

DEAD LOAD DEFORMATION TEST

All of the products tested were manufactured using a high shear, double arm mixer heated to 200° C. Inert gas was used throughout the processing to minimize degradation.

Samples taken from each batch were pressed between release paper using a Carver laboratory press. The release paper was heated in a forced air oven to 200° C. for 15 minutes to drive out residual moisture. The press was equipped with heated jaws set at 200° C. and was shimmed to yield an adhesive thickness of 50 micrometers.

A dwell time of approximately 5 seconds at $3.5 \times 10^6$ Kg/m$^2$ was generally sufficient to form an air-free film.

A dumbbell-shaped specimen was cut from the essentially air-free films using a standard striking die.

Marks were placed on the reduced section of each specimen approximately equidistant from its center and perpendicular to its longitudinal axis. The centers of the marks were 25.0 mm±0.5 mm apart.

Each specimen was fastened in a vertical position at test temperature and weights equaling 1500 gms/cm$^2$ of cross sectional area were attached. Each specimen was conditioned in this mode for a period of 3 hours. After 3 hours, the weights were removed and each specimen was allowed to retract and equilibrate at 25° C. for 5 minutes. The distance between marks was remeasured and the percent "dead load creep" or elongation (permanent longitudinal deformation or set) was calculated as follows:

Elongation percent = $L_2 - L_1 L_1 \times 100\%$ wherein $L_2$ = measured distance bedtween marks on the conditioned specimen, and $L_1$ = original distance between marks, and the original sample is greater than 25 mm in length.

This procedure is a modification of A.S.T.M. D-412 (tension testing of vulcanized rubber) and the dumbbell-shaped samples were formed using Die C.

The dead load deformation data from Examples I, III, IV, and V are set forth below.

TABLE III

| PERMANENT DEFORMATION FROM 1500 g/cm$^2$ AT VARIOUS TEMPERATURES | | | | |
|---|---|---|---|---|
| Example | Room Temperature | 37.8° C. | 43.3° C. | 48.9° C. |
| I | 2% | 4% | 8% | 8% |
| III | 2% | 10% | 30% | 30% |
| IV | 2% | 10% | 24% | 36% |
| V | 6% | 34% | 56% | 74% |

In the case of Example V, some temperature dependency of G", G', and loss tangent should be noted at 0.25 Hz, and the deformation data are believed to reflect a similar temperature dependency. Furthermore, G' at 0.01 Hz was considered marginal for this formula.

The data for Examples I-14 V are believed to establish that a variety of relatively high molecular weight, relatively high vinyl-arene elastomeric block copolymers can be used in this invention, e.g. both the radial and linear types. Blends of these various types of block copolymers (e.g. 1/99—99/1) will provide suitable elastic bases for admixture with endblock and midblock resins or materials. Examples I-V are also believed to demonstrate the value of a good balance between high softening endblock associating resin and midblock associating resin in the preferred compositions.

Samples of Examples I-V were tested for tensile strength at 500% elongation at room temperature (20°-25° C.). It was found that the tensile strength exceeded 35,000 Kg/m$^2$ for all samples. For Examples I-IV, this measurement was significantly higher, generally in excess of 70,000 Kg/M, indicating good cohesiveness.

To provide a further standard of comparison for the rheological data obtained from Examples 1-5, data regarding untackified, unextended, linear A-B-A block copolymers (e.g. of the KRATON ® type) were obtained for 0.25 Hz/room temperature conditions. These data indicate that G' is typically above 300×10$^4$ dynes/cm$^2$ and G" is typically above 50×10$^4$ dynes/cm$^2$ and even, in some cases, above 100×10$^4$ dynes/cm$^2$. Like vulcanized natural rubber, these block copolymers exhibit excellent elastomeric behavior but, in the absence of tackifying resins, exhibit little adhesive behavior.

The description and Examples above are a basis for understanding and using the invention. However, since many embodiments can be made without departing from the spirit and scope of the invention, the invention resides solely in the claims hereinafter appended.

We claim:

1. A method for imparting elastic properties to a flexible substrate, which comprises contacting a surface of the flexible substrate with a band of a self-adhering elastic composition which consists essentially of:
   (a) a block copolymer comprising at least one substantially amorphous, rubbery polymeric midblock and at least was glassy poly(vinylarene) end blocks;
   (b) about 20 to 150 parts by weight of a midblock associating resin; and
   (c) about 10 to 50 parts by weight of an endblock associating resin having a glass transition temperature and a softening point above about 115° C. each per 100 parts of the block copolymer;
   wherein the proportions of components (a), (b), and (c) are selected to provide the following properties:
   (i) a tensile strength at 500% elongation, determined at 20°-25° C., of at least 50 pounds per square inch;
   (ii) a 180° peel resistance, according to PSTC-1, determined at 20°-25° C. 24 hours after formation of the pressure-sensitive adhesive bond, of at least about 450 grams per 25.4 mm-width;
   (iii) a dead load deformation, tested at 37.8° C. and 1500 g/cm$^2$, less than 50%; and
   (iv) a loss modulus of 5×10$^4$ to 100×10$^4$ dynes/cm$^2$, a storage modulus of 65×10$^4$ to 225×10$^4$ dynes/cm$^2$, and a loss tangent of 0.03 to 1.0, at 0.01-0.25 Hz at 25°-50° C.

2. The method of claim 1 wherein the flexible substrate is substantially inelastic.

3. The method of claim 1 wherein the flexible substrate is pre-gathered.

4. The method of claim 1 wherein prior to contacting the band with the flexible substrate the band is formed by extruding the self-adhering elastic composition at a temperature above its endblock Tg, and cooling the extruded band to a temperature below its endblock Tg but above its midblock Tg.

5. The method of claim 4 wherein the band is simultaneously cooled and contacted with the flexible substrate.

6. The method of claim 1 wherein the band is placed under tension, at a temperature below its endblock Tg, in such a manner that the band is elongated when contacted with the surface of the flexible substrate.

7. The method of claim 1 wherein the band is continuously contacted with the surface of the flexible substrate.

8. The method of claim 1, wherein the flexible substrate comprises a polymeric film or a woven or nonwoven web, less than 3 mm thick.

9. The method of claim 1 wherein:
   (a) the block copolymer comprises at least one substantially amorphous midblock, and at least two poly(vinylarene) endblocks, and
   (b) about 20 to 150 parts by weight of the midblock associating resin; and
   (c) about 10 to 150 parts by weight of the endblock associating resin comprising an aromatic, essentially hydrocarbon endblock associating resin having a Tg and a softening point greater than the copolymer endblocks and the midblock associating resin, each per one hundred parts by weight of component (a).

10. The method of claim 9 wherein the self-adhering elastic has the following rheological properties at a temperature of about 25°-50° C.:

| | 0.01 Hz | 0.25 Hz |
|---|---|---|
| loss modulus, 10$^4$ dynes/cm$^2$ | 5–25 | 10–100 |
| storage modulus, 10$^4$ dynes/cm$^2$ | 75–200 | 75–200 |
| loss tangent | 0.05–0.3 | 0.08–1.0 |

11. The method of claim 10 wherein said rheological properties are as follows:

|  | 0.01 Hz | 0.25 Hz |
| --- | --- | --- |
| loss modulus, $10^4$ dynes/cm$^2$ | 8–16 | 15–35 |
| storage modulus, $10^4$ dynes/cm$^2$ | 100–175 | 120–200 |
| loss tangent | 0.07–0.10 | 0.1–0.25. |

12. The method of claim 1 wheein the dead load deformation of said self-adhering elastic, at 37.8° C. for 3 hours, and 1500 g/cm$^2$ of cross section, is less than about 50%.

13. The method for imparting a self-adhering elastic to a flexible substrate comprising the steps of:
  (a) unreeling a band of self-adhering elastic composition from a roll, said roll being maintained at a temperature below the softening point of said self-adhering elastic and said band of self-adhering elastic being an extrudate at least 50 microns in thickness which consists essentially of a block copolymer comprising at least one substantially amorphous, rubbery polymeric midblock and at least two glassy poly(vinylarene) end blocks; (ii) 20–150 parts per hundred of a midblock associating resin; and (iii) 10–150 parts per hundred of an aromatic, essentially hydrocarbon endblock associating resin having a Tg and a softening point above 115° C. each per one hundred parts of the block copolymer; wherein the proportions (i), (ii), and (iii) are selected to provide the following properties:
    (i) a tensile strength at 500% elongation, determined at 20°–25° C., of at least 50 pounds per square inch;
    (ii) at 180° peel resistance, according to PSTC-1, determined at 20°–25° C. 24 hours after formation of the pressure-sensitive adhesive bond, of at least about 450 grams per 25.4 mm-width;
    (iii) a dead load deformation, tested at 37.8° C. and 1500 g/cm$^2$, less than 50%; and
    (iv) a loss modulus of $5 \times 10^4$ to $100 \times 10^4$ dynes/cm$^2$, a storage modulus of $65 \times 10^4$ to $225 \times 10^4$ dynes/cm$^2$, and a loss tangent of 0.03 to 1.0, at 0.01–0.25 Hz at 25°–50° C.
  (b) contacting the band of self-adhering elastic with a surface of a flexible substrate forming a bond between the substrate and elastic.

14. The method of claim 13 wherein the substrate is substantially inelastic.

15. The method of claim 13 wherein the band is placed under tension in such a manner that it is elongated when contacted with the flexible substrate.

16. The method of claim 13 wherein the band has a backing.

17. The method of claim 16, wherein the backing of the band comprises a release liner which is removed from the band prior to contacting the band with the flexible substrate.

18. The method of claim 16, wherein the backing of the band is substantially elastomeric.

19. The method of claim 16 wherein the self-adhering elastic has been formed by coextruding the backing and the band, and wherein the backing has release characteristics.

20. An article which comprises a product of the method of claim 1 or 13.

21. The article of claim 20 which comprises a disposable diaper.

* * * * *

UNITED STATES PATENT AND TRADEMARK OFFICE
CERTIFICATE OF CORRECTION

PATENT NO. : 4,418,123

DATED : November 29, 1983

INVENTOR(S) : WILLIAM L. BUNNELLE and RICHARD C. LINDMARK

It is certified that error appears in the above-identified patent and that said Letters Patent are hereby corrected as shown below:

```
Column 4, line 23, for "defind" read --defined--.
Column 4, line 61, for "trangent" read --tangent--.
Column 7, line 32, for "block" read --blocks--.
Column 10, line 19, for "coolymer" read --copolymer--.

Column 13, line 16, for "wegit" read --weight--.
Column 13, line 68, for "wil" read --will--.
Column 17, line 8, for "0.5" read --0.25--.
Column 18, line 21, for "defomation" read --deformation--.
Column 18, line 67, for "bedtween" read --between--.
Column 19, line 66, for "was" read --two--.
Column 20, line 1, for "10 to 50" read --10 to 150--.
Column 21, line 8, for "wheein" read --wherein--.
Column 21, line 19, for "essentially of a" read
   --essentially of (i) a--.
```

Signed and Sealed this

Twenty-seventh Day of August 1985

[SEAL]

Attest:

DONALD J. QUIGG

Attesting Officer

Acting Commissioner of Patents and Trademarks